United States Patent
Chan et al.

(10) Patent No.: US 9,452,281 B2
(45) Date of Patent: Sep. 27, 2016

(54) TATTOOING SYSTEMS AND METHODS

(71) Applicant: Elwha LLC, Bellevue, WA (US)

(72) Inventors: Alistair K. Chan, Bainbridge Island, WA (US); Roderick A. Hyde, Redmond, WA (US); Jordin T. Kare, Seattle, WA (US); David B. Tuckerman, Lafayette, CA (US); Lowell L. Wood, Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

(21) Appl. No.: 13/874,006

(22) Filed: Apr. 30, 2013

(65) Prior Publication Data

US 2014/0324089 A1    Oct. 30, 2014

(51) Int. Cl.
*A61B 17/34* (2006.01)
*A61M 37/00* (2006.01)

(52) U.S. Cl.
CPC .................... *A61M 37/0076* (2013.01)

(58) Field of Classification Search
CPC ............. A61B 17/3417; A61B 5/0531
USPC ............. 606/116, 185, 186; 81/9.22; 30/362
See application file for complete search history.

(56) References Cited

U.S. PATENT DOCUMENTS

| | | | |
|---|---|---|---|
| 4,204,438 A * | 5/1980 | Binaris et al. | 81/9.22 |
| 5,401,242 A * | 3/1995 | Yacowitz | 604/48 |
| 5,445,611 A | 8/1995 | Eppstein et al. | |
| 6,135,994 A | 10/2000 | Chernoff | |
| 6,341,831 B1 * | 1/2002 | Weber et al. | 347/1 |
| 6,726,693 B2 | 4/2004 | Weber et al. | |
| 6,764,493 B1 | 7/2004 | Weber et al. | |
| 6,890,319 B1 * | 5/2005 | Crocker | 604/131 |
| 6,980,855 B2 | 12/2005 | Cho | |
| 7,207,242 B1 * | 4/2007 | Daigle | 81/9.22 |
| 2002/0058952 A1 | 5/2002 | Weber et al. | |
| 2002/0193754 A1 | 12/2002 | Cho | |

(Continued)

OTHER PUBLICATIONS

Cash et al., "Two- and three-dimensional ultrasound in the development of a needle-free injection system", The British Journal of Radiology, Mar. 2004, vol. 77, pp. 236-242.

(Continued)

*Primary Examiner* — Richard Louis
(74) *Attorney, Agent, or Firm* — Foley & Lardner LLP

(57) ABSTRACT

A tattooing apparatus including a needle having at least one tip. The needle is configured to move between a first position in which the tip is located above the surface of a skin, and a second position in which the tip is located at a penetration depth underneath the skin surface. The needle is further configured to deposit an ink between the skin surface and the penetration depth. The tattooing apparatus further includes a needle drive mechanism configured to move the needle between the first position and the second position. The tattooing apparatus includes a sensor configured to output a feedback signal corresponding to a skin thickness characteristic. The tattooing apparatus further includes a controller configured to receive the feedback signal, wherein the controller is configured to adjust the penetration depth based on the skin thickness characteristic.

30 Claims, 12 Drawing Sheets

(56) References Cited

U.S. PATENT DOCUMENTS

| | | |
|---|---|---|
| 2004/0186419 A1 | 9/2004 | Cho |
| 2004/0267121 A1* | 12/2004 | Sarvazyan et al. ............ 600/439 |
| 2005/0163711 A1 | 7/2005 | Nycz et al. |
| 2007/0032846 A1* | 2/2007 | Ferren et al. .................... 607/89 |
| 2007/0208363 A1 | 9/2007 | Lai |
| 2008/0033356 A1* | 2/2008 | Kluge et al. ................... 604/117 |
| 2008/0195043 A1* | 8/2008 | Schwach et al. ............. 604/116 |
| 2008/0247637 A1* | 10/2008 | Gildenberg ................... 382/153 |
| 2008/0300615 A1* | 12/2008 | Colton et al. ................. 606/186 |
| 2009/0209899 A1 | 8/2009 | Unger et al. |
| 2009/0227994 A1* | 9/2009 | Grundfest et al. ................ 606/9 |
| 2010/0030111 A1* | 2/2010 | Perriere ........................ 600/583 |
| 2011/0118698 A1 | 5/2011 | Eckhoff et al. |
| 2011/0150765 A1 | 6/2011 | Boyden et al. |
| 2011/0230833 A1* | 9/2011 | Landman et al. ............ 604/117 |

OTHER PUBLICATIONS

Dermcup: High resolution ultrasound scanner for skin imaging, from atysmedical.fr(www.atysmedical.fr/en/pages/products/dermcup.php), retrieved on May 1, 2013, 6 pages.

Quintavalle, Paul R., "Getting a Better View With High Resolution Ultrasound", Podiatry Today, Oct. 2002, vol. 15, Issue 10, 2 pages.

Reinholdt Petersen et al., "High-frequency ultrasound measurement of dermis and subcutaneous fat in the newborn infant" onlinelibrary, May 1995, vol. 1, Issue 2, pp. 86-89.

Schmid-Wendtner, M. H. et al., "Ultrasound Scanning in Dermatology", Arch Dermatol, Feb. 2005, vol. 141, pp. 217-224.

Ultrasound Guide for Emergency Physicians, from sonoguide.com (http://sonoguide.com/soft_tissue.html), retrieved on May 1, 2013, 8 pages.

Welzel et al., OCT in Dermatology, Apr. 2008, 20 pages.

* cited by examiner

TATTOOING SYSTEMS AND METHODS

BACKGROUND

Creating a permanent or near permanent tattoo on a person requires placing indelible ink into the dermis layer of the skin. The indelible ink is generally permanent and is not absorbed by the body or transported out of the body when placed in the dermis layer of the skin. The ink is placed into the dermis through a needle, which is generally part of a tattooing machine, often called a tattoo gun. The needle often contacts nerve endings, which can cause pain for the tattoo recipient.

Generally, tattoo machines operate by oscillating at least one needle at a rapid speed (e.g., 80 to 150 times per second) into and out of a person's skin. The needle's penetration may be adjustable, but generally, the needle penetrates between 1 mm and 4 mm beneath the surface of the skin. The needle carries ink and deposits the ink into the person's skin. Tattoo machines typically come in two primary variations: coil machines and rotary machines. Coil tattoo machines utilize electromagnetic coils with springs that oscillate an arm up and down, which drives the needle oscillation. A rotary tattoo machine uses a motor and a cam, which drives the needle oscillation. In both machines, the needle penetration depth remains generally the same during a single use. Manual adjustments between tattooing operations work to vary the needle penetration depth.

SUMMARY

One exemplary embodiment relates to a tattooing apparatus. The tattooing apparatus includes a needle having at least one tip. The needle is configured to move between a first position in which the tip is located above the surface of a skin, and a second position in which the tip is located at a penetration depth underneath the skin surface. The needle is further configured to deposit an ink between the skin surface and the penetration depth. The tattooing apparatus further includes a needle drive mechanism configured to move the needle between the first position and the second position. The tattooing apparatus includes a sensor configured to output a feedback signal corresponding to a skin thickness characteristic. The tattooing apparatus further includes a controller configured to receive the feedback signal, wherein the controller is configured to adjust the penetration depth based on the skin thickness characteristic.

Another exemplary embodiment relates to a method of tattooing. The method includes configuring a tattooing system with a setting corresponding to a layer of skin where an ink is to be deposited. The method further includes causing a needle to oscillate in and out of a skin at a penetration depth such that the needle deposits the ink into the layer of skin. The method includes causing an adjustment to the penetration depth in response to a feedback signal from a sensor. The sensor feedback signal indicates a detected change in depth of the layer of skin from a surface of the skin. The adjustment is such that the needle continues to deposit the ink into the layer of skin.

A further exemplary embodiment relates to a tattooing system. The tattooing system includes a sensor unit configured to provide skin data corresponding to an area of skin. The skin data includes data corresponds to at last one of a layer thicknesses and a layer depth of the area of skin. The tattooing system further includes a tattoo unit, wherein the tattoo unit is separate from the sensor unit. The tattoo unit includes a needle having at least one tip. The needle is configured to move between a first position in which the tip is located above a surface of the skin, and a second position in which the tip is located at a penetration depth underneath the skin surface. The needle is further configured to deposit an ink between the skin surface and the penetration depth. The tattoo unit further includes a needle drive mechanism configured to move the needle between the first position and the second position. The tattoo unit includes a tattoo unit position sensor configured to output a signal corresponding to a position of the tattoo unit on the area of skin. The tattoo unit includes a controller configured to adjust the penetration depth based on the position of the tattoo unit and on the skin data.

Yet another exemplary embodiment relates to a method of tattooing. The method includes transferring skin data from a sensor unit to a tattoo unit. The skin data corresponds to depth and thickness measurements for at least one layer of a skin across an area to be tattooed. The sensor unit creates the skin data by scanning the area to be tattooed with a sensor. The method further includes providing a setting corresponding to a location within the skin where an ink is to be deposited. The method includes causing a needle of the tattoo unit to oscillate in and out of the skin at a penetration depth such that the needle deposits the ink into the skin at the location within the skin. The method further includes causing an adjustment to the penetration depth in response to a result of a comparison of a position of the tattoo unit with the skin data that indicates that a depth of the location within the skin has changed such that the needle continues to deposit the ink at the location of the skin.

The invention is capable of other embodiments and of being carried out in various ways. Alternative exemplary embodiments relate to other features and combinations of features as may be generally recited in the claims.

The foregoing is a summary and thus by necessity contains simplifications, generalizations, and omissions of detail. Consequently, those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Figure 1A:
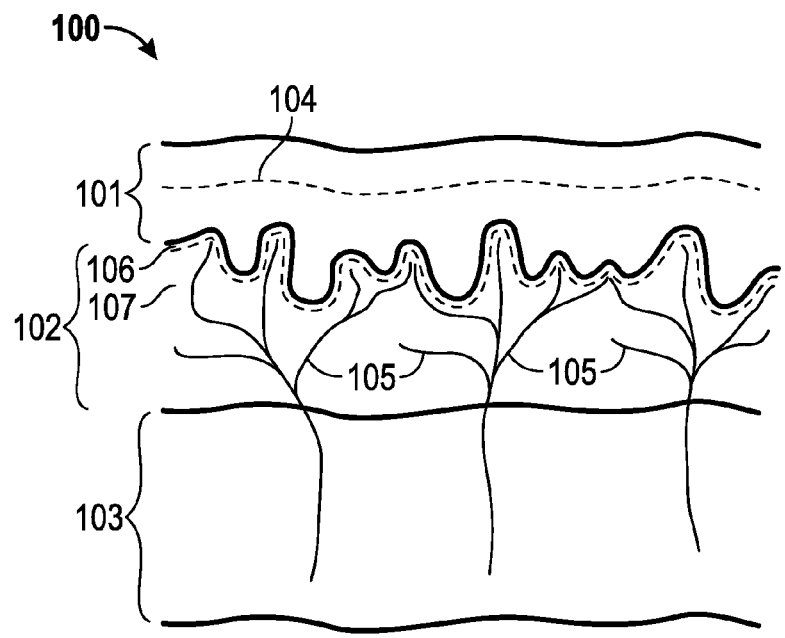
FIG. 1A is a simplified schematic view of layers of skin.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Referring to FIG. 1, a simplified schematic view of skin 100 is shown. Skin 100 is comprised of three main layers: epidermis 101, dermis 102, and hypodermis 103. Epidermis 101 represents the outer layer of skin and generally includes outer layers and inner layers, as shown by dividing line 104. Epidermis skin cells are formed in the inner layers and move outward toward the outer layers where the cells fall off of the body in a process known as keratinization. Epidermis 101 is in a constant state of flux and epidermis skin cells are not permanent cells within the body. Tattoo ink placed in epidermis 101 eventually leaves the body as it moves from the inner layers, to the outer layers, and off of the body through the keratinization process. The thickness of epidermis 101 varies across different locations of the body (e.g., an average thickness of approximately 0.05 mm at the eyelids and approximately 1.5 mm on the palms and soles). Further, even within these locations, as shown by FIG. 1, the transition between epidermis 101 and dermis 102 varies such that the thickness of epidermis 101 is not constant within the same area of skin 100. Still further, the thickness of epidermis 101 can vary from person to person.

Dermis 102 contains generally permanent skin cells that do not experience keratinization. Accordingly, tattoo ink is ideally placed in dermis 102 because the ink will not be carried away and off the body. However, unlike epidermis 101, dermis 102 includes nerve endings 105. Dermis 102 also includes blood vessels (not shown) that provide nutrients to dermis 102 and epidermis 101. Nerve endings 105 do not extend into epidermis 101. Dermis 102 also includes multiple sub-layers, notably: papillary region 106, which is closest to epidermis 101, and reticular region 107, which is beneath papillary region 106. Papillary region 106 contains minimal nerve endings 105.

Figure 1B:
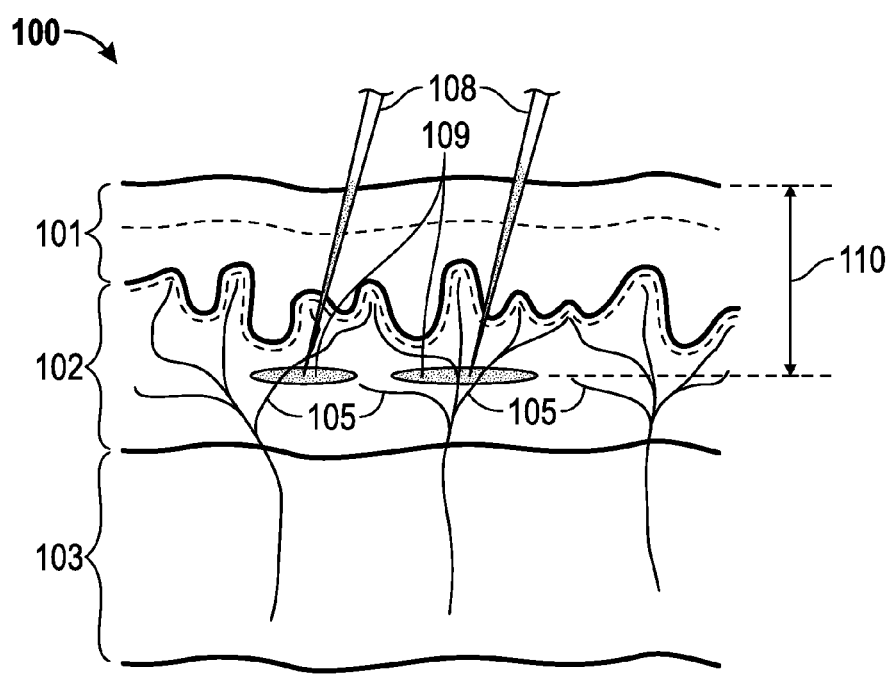
FIG. 1B is a schematic view of a tattoo needle placing ink within skin.

Referring to FIG. 1B, during that tattooing process, needle 108 delivers ink 109 to dermis 102. Needle 108 deposits ink 109 at a generally constant depth 110 from the surface of skin 100 such that all or a majority of the ink is deposited into dermis 102 and none or little ink is deposited into epidermis 101 or hypodermis 103. Needle 108 is configured to deposit ink at a depth proximate to the penetration depth. Any ink deposited into epidermis 101 will eventually leave the skin through keratinization. In a conventional approach, depth 110 may correspond to the outermost layers of dermis 102 (e.g., papillary region 106) because both the thicknesses and depths of epidermis 101 and dermis 102 vary. Accordingly, in such a conventional approach, needle 108 may plunge deeper into dermis 102 than necessary and contact nerve endings 105 causing pain. Further, where epidermis 101 is thick, needle 108 may remain in epidermis 101, resulting in elimination of ink 109 over time.

Figure 2A:
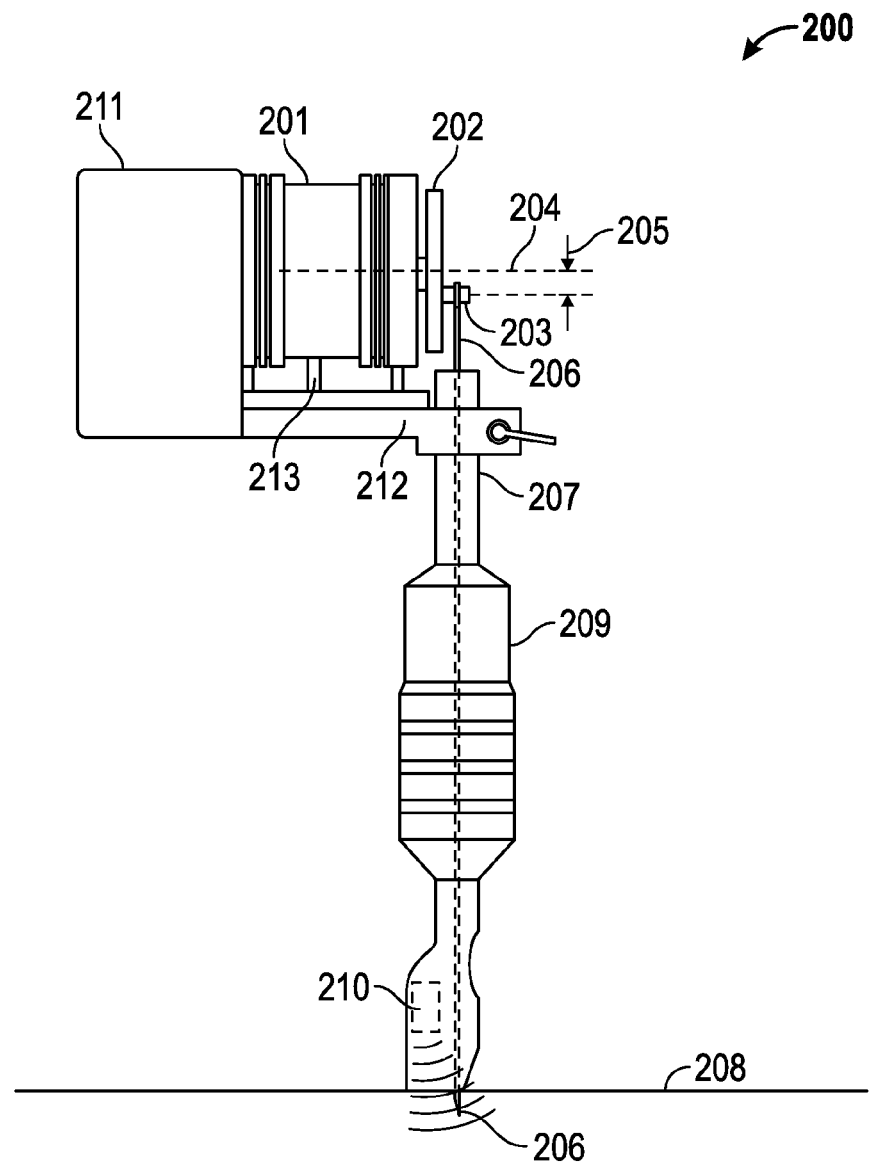
FIG. 2A is a schematic view of a first exemplary tattoo machine.

Referring to FIG. 2A, a rotary tattoo system 200 is shown according to an exemplary embodiment. System 200 includes motor 201 that spins a cam wheel 202. Cam wheel 202 includes an offset shaft 203 that is offset from the rotational axis 204 of motor 201 by a distance 205. A first end of needle 206 is attached to offset shaft 203, the main shaft of needle 206 is received in needle tube 207, and the second end of needle 206 oscillates in and out of needle tube 207. The second end of needle 206 oscillates between a first position, in which the second end of needle 206 is completely contained within needle tube 207, and a second position, in which the second end of needle 206 at least partially protrudes from needle tube 207 by a skin penetration depth. In some arrangements, system 200 may not include a tube but still include a skin guide (e.g., a plate sitting on the surface of skin 208) in which case needle 206 oscillates between a first position in which the tip of the needle is located on one side of the aperture (e.g., not penetrating the skin) and a second position in which the tip of the needle is located on the other side of the aperture (e.g., penetrating the skin). Accordingly, as motor 201 spins, offset shaft 203 raises and lowers by distance 205 above and below rotational axis 204, which oscillates needle 206 in and out of needle tube 207. During tattooing operations, needle 206 repeatedly penetrates skin 208 at the penetration depth and deposits ink within skin 208. Although needle 206 is shown as a single needle point, it is contemplated that any tattoo needle configuration may be used, including multiple needle points mounted to a single shaft. For example, needle 206 may include a plurality of needles arranged in any of a liner, a shader, or a flat arrangement. Needle tube 207 includes user grip 209 such that a tattoo artist can comfortably hold system 200.

System 200 includes sensor 210. Sensor 210 is configured to scan skin 208 at the point where needle 206 penetrates skin 208, or at a location proximate thereto. Sensor 210 provides a feedback signal to controller 211. Controller 211 is mounted to needle tube 207 through platform 212. In other embodiments, controller 211 is located in other locations, including locations remote to the rest of the system. The feedback signal relates to detected depths and thicknesses of certain layers of skin. Sensor 210 is configured to detect the depth and thickness of the person's epidermis, dermis, and hypodermis. Further, sensor 210 is configured to detect sub-layer depths and thicknesses within the major layers of the person's skin. For example, sensor 210 may determine the depth and thickness of the papillary region and the reticular region of the person's dermis at the point of needle penetration. Controller 211 analyzes the feedback signal from sensor 210 to determine the optimal needle penetration depth. Needle penetration depth is adjusted during use such that ink is consistently deposited within a particular layer of skin 208, within a particular sub-layer of a layer of skin 208, at a specific depth beneath the surface of a layer of skin 208, within a range of a particular layer of skin 208, or at a consistent percentage of a thickness of a skin layer (e.g., at a depth of 30% of the dermis layer). Needle penetration depth is adjusted by moving motor 201 and cam wheel 202 vertically up and down in small increments in relation to needle tube 207. Accordingly, lift mechanism 213 is provided between motor 201 and platform 212 such that motor 201 and cam wheel 202 can be displaced vertically with respect to needle tube 207. Lift mechanism 213 is capable of raising and lowering motor 201 and cam wheel 202 in precise amounts (e.g., 10 or 100 μm at a time). Lift mechanism 213 may be any of a linear actuator, a piezoelectric linear actuator, a multi-layer piezoelectric linear actuator, a screw-driven actuator driven by a stepper motor, or a combination of any of the above. The operation of lift mechanism 213 is controlled by controller 211 based on an operator programmed tattooing parameters and settings (e.g., ink placement target or strategy). It is readily apparent that alternative methods beyond those illustrated in FIG. 2A can be used to vary the needle penetration depth. In an alternative embodiment, the needle penetration depth is adjusted by changing the distance 205 between rotational axis 204 and offset shaft 203. In another alternative embodiment, the needle penetration depth is adjusted by varying the length of the needle tube 207. In such an alternative embodiment, the length variation of needle tube 207 may be implemented by sliding needle tube 207 relative to platform 212, or may be implemented using variable spacers between the base of the needle tube and skin 208.

In one embodiment, sensor 210 utilizes optical coherence tomography to detect skin 208 layer depths and thicknesses. A more detailed explanation of utilizing optical coherence tomography to detect skin characteristics is described in "OCT in Dermatology," by J. Welzel et al., which is incorporated herein by reference in its entirety. Accordingly, sensor 210 emits a near-infrared light beam into skin 208. The light source may be any of a superluminescent diode, an ultra-short pulsed laser, a supercontinuum laser, or other coherent light sources. The emitted light penetrates skin 208 and a portion of the light reflects back to sensor 210 at varying depths within skin 208. The light reflects back and scatters at different rates and in different quantities depending on various factors of the skin material (e.g., material density) the light travels through or is reflected by. Accordingly, controller 211 receives a feedback signal from sensor 210 and uses the data contained within the feedback signal to locate the depths and thicknesses of the different layers of skin 208. Controller 211 is configured to adjust lift mechanism 213 such that needle 206 penetrates to the appropriate depth as defined by the provided tattooing parameters and settings based on the feedback signal.

In an alternative arrangement, sensor 210 utilizes ultrasound to detect skin 208 layer depths and thicknesses. A more detailed explanation of utilizing ultrasound to detect skin characteristics is described in "High-frequency ultrasound measurement of dermis and subcutaneous fat in the newborn infant," by Jes Reinhold Peterson et al., which is incorporated herein by reference in its entirety. Accordingly, sensor 210 emits pulses of ultrasonic sound waves. The sound waves may be longitudinal waves (e.g., to measure density variations) or shear waves (e.g., to measure elasticity variations). As the sound waves travel through skin 208 tissue, a portion of the sound waves reflect back to sensor 210 at various strengths depending on the density or elasticity of skin 208 tissues. Accordingly, because the different layers of skin 208 have different densities and elasticities, sensor 210 is used to detect both the depth and thickness of each layer of skin 208. In another alternative arrangement, sensor 210 utilizes conductivity and/or resistance to detect skin 208 layer depths and thicknesses. Each layer of skin 208 has a slightly different electrical resistance. Accordingly, sensor 210 may send a small electric pulse across an area of skin, measure the resistance, and determine what layers and how much or each layer is present across the path of the electric pulse.

Figure 2B:
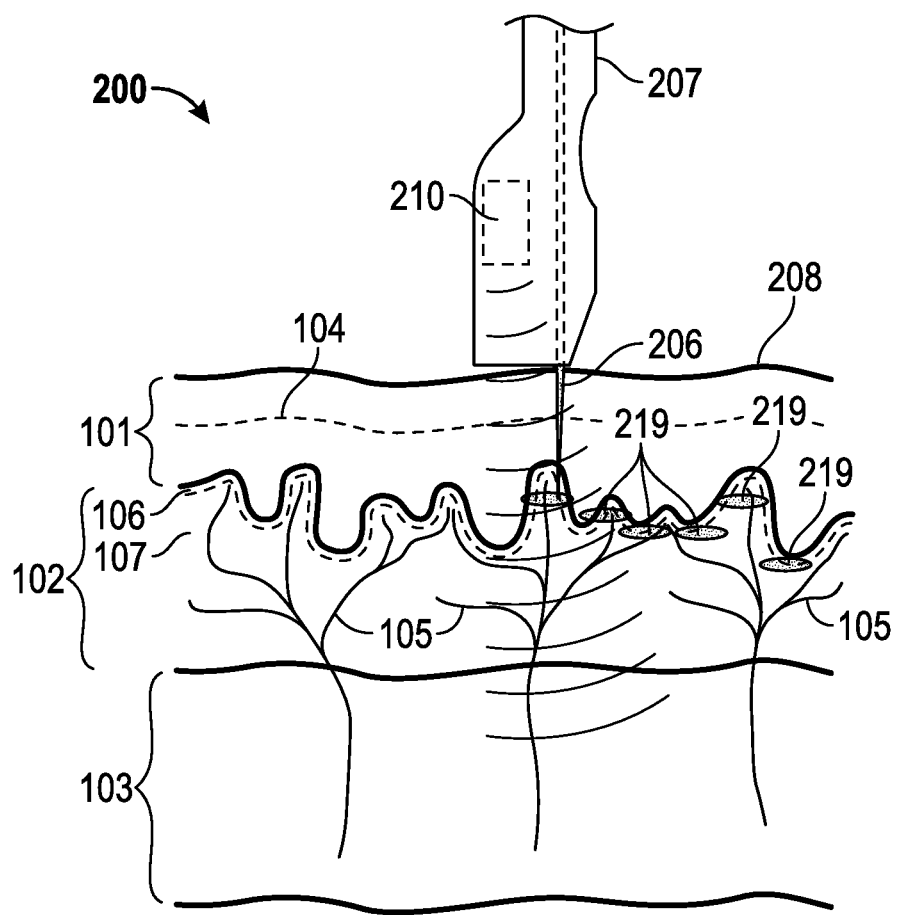
FIG. 2B is a schematic view of a tattoo needle of the first exemplary tattoo machine placing ink within skin.

Referring to FIG. 2B, a magnified view of needle penetration into skin 208 is shown. Sensor 210 actively scans skin 208 to detect the depths and widths of various layers and sub-layers of skin (e.g., epidermis 101, dermis 102, hypodermis 103, papillary region 106, and reticular region 107). As shown in FIG. 2B, as needle 206 moves along skin 208, penetration depth of needle 206 is adjusted to deposit ink 219 at varying depths. The varying depth may correspond to a set distance beneath the surface of a layer (e.g., 0.1 mm below surface of dermis 102), within a specific layer or sub-layer (e.g., within papillary region 106), between two layers (e.g., between epidermis 101 and dermis 102), within a range of a particular layer of skin, or at a consistent percentage of a thickness of a skin layer (e.g., 30% deep into reticular region 107). By actively adjusting needle penetration depth, needle 206 may impact fewer nerve endings 105 than a traditional tattoo machine (see, e.g., FIG. 1B).

As discussed above, needle depth is actively adjusted as system 200 moves along skin 208. Needle penetration depth is adjusted with each oscillation. Alternatively, needle penetration depth is adjusted every set number of oscillations (e.g., every tenth oscillation or every 100th oscillation). In yet another alternative, needle penetration depth is adjusted based on detected movement of system 200 along skin 208. Accordingly, system 200 may include a movement or position sensor in addition to sensor 210 (or integrated within sensor 210) that detects system 200 displacement along skin 208. It is contemplated that needle penetration depth may be adjusted after displacement by a set lateral distance, such as once every centimeter of system 200 movement along skin 208. It is contemplated that needle penetration depth may be adjusted in response to changes in the thickness or depths of skin layers. For example, the needle penetration depth may be adjusted when the changes in the thickness or depths of skin layers exceed a designated threshold.

Figure 2C:
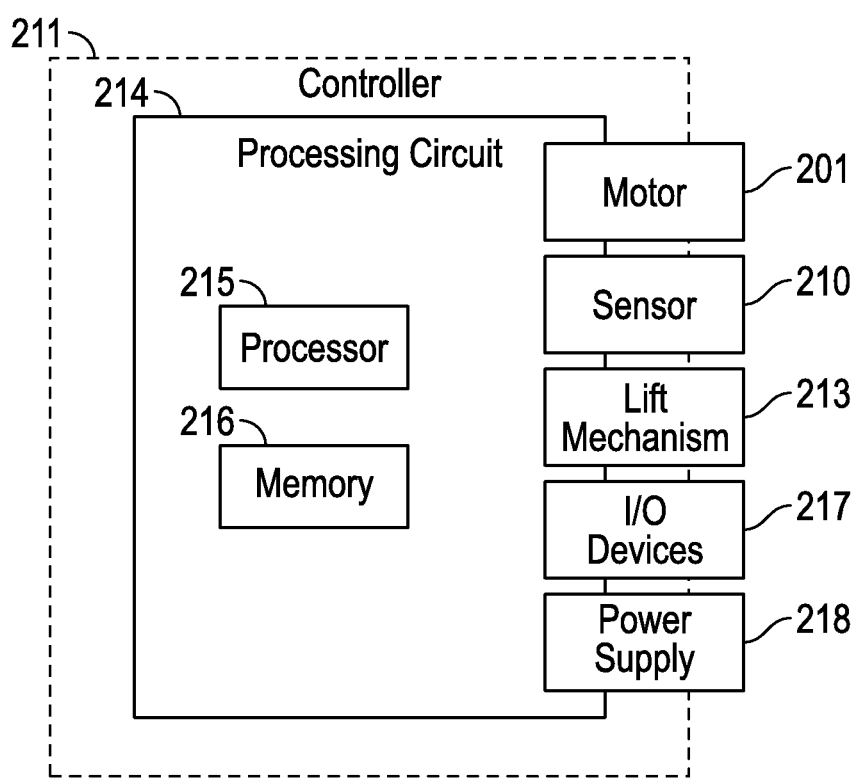
FIG. 2C is a block diagram of the first exemplary tattoo machine.

Referring to FIG. 2C, a block diagram of controller 211 is shown. Controller 211 includes processing circuit 214. Processing circuit includes processor 215 and memory 216. Processing circuit 214 communicates with motor 201, sensor 210, lift mechanism 213, and input/output devices 217. Controller 211 and the components of system 200 are powered by power supply 218. Memory 216 stores necessary programming modules that, when run by processor 215, control the operation of system 200 based on desired user settings received through input/output devices 217 and skin 208 layer depth and thickness information received from sensor 210. Input/output devices 217 are configured to provide an interface for a user to input desired tattooing parameters and settings for system 200. It is contemplated that input/output devices 217 include a series of knobs, wheels, or multi-position switches (e.g., a knob, wheel, or switch for each of motor 201 speed, desired skin 208 layer for ink 219 placement, a depth within the desired skin 208 layer, and any other tattooing parameter or setting). Alternatively, input/output devices 217 may include a touch screen including an interactive graphical user interface such that a user of system 200 can program the desired ink 219 placement and motor 201 speed parameters. Still further, it is contemplated that input/output devices 217 may communicate with an external computing device that may be programmed by a user of system 200 (e.g., a laptop, a PDA, a smartphone, a tablet, etc.). Accordingly, the user may select the desired tattooing parameters on the external computing device and transmit the desired parameters to controller 211 via a wired or a wireless connection (e.g., Bluetooth, WiFi, etc.). Alternatively, tattooing parameters and settings are stored on removable storage media (e.g., SD, MicroSD, USB flash, etc.) and the removable storage media is provided to controller 211 through input/output devices 217. In yet another alternative, it is contemplated that memory 216 stores various tattooing templates (e.g., templates for tattooing in specified layers of skin, templates for tattooing on specified body areas, etc.). Input/output devices 217 further include an on/off mechanism (e.g., a foot pedal or a hand operated trigger or button) such that the operator of system 200 may control the oscillation of needle 206. The on/off mechanism may be capable of instructing variable speeds for motor 201 (e.g., a pressure sensitive foot pedal or hand trigger). Power supply 218 provides power to system 200. Power supply 218 may receive power from any suitable source (e.g., a rechargeable battery, a non-rechargeable battery, grid power, etc.).

Figure 3A:
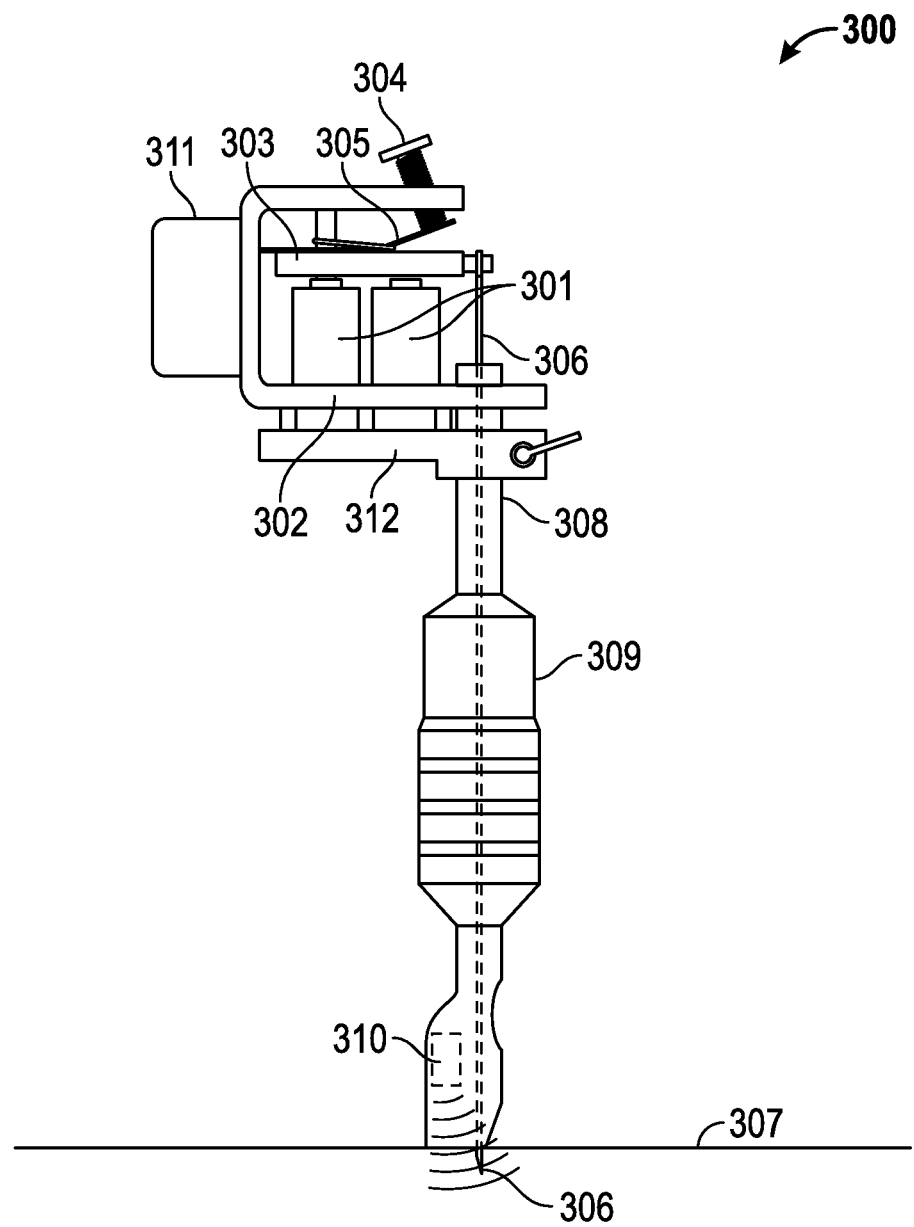
FIG. 3A is a schematic view of a second exemplary tattoo machine.

Referring to FIG. 3, an electromagnetic coil tattoo system 300 is shown. System 300 is similar to system 200 and operates on the same general principles and includes similar features. However, the needle drive mechanism of system 300 is different than the needle drive mechanism of system 200. System 300 includes electromagnetic coils 301 instead of motor 201 and cam wheel 202. Electromagnetic coils are mounted to frame 302. Frame 302 includes spring loaded armature 303, which is biased away from electromagnetic coils 301. Frame 302 further includes contact screw 304. Armature 303 further includes electrical contact 305. In operation, when screw 304 contacts electrical contact 305, electromagnetic coils 301 receive power and create a magnetic field that attracts armature 303 towards electromagnetic coils 301. As armature 303 moves toward electromagnetic coils 301, armature 303 drives needle 306 into skin 307. Further, as armature 303 moves towards electromagnetic coils 301, screw 304 and electrical contact 305 separate, opening the electric circuit powering electromagnetic coils 301. Accordingly, electromagnetic coils 301 turn off, and armature 303, which is spring-biased away from electromagnetic coils 301, moves away from electromagnetic coils 301 and pulls needle 306 out of skin 307. As armature 303 moves away, screw 304 and electrical contact 305 touch, the electric circuit is closed, and the electromagnetic coils 301 are reactivated. This process repeats as long as electricity is supplied to electromagnetic coils 301. A first end of needle 306 is attached to armature 303, the main shaft of needle 306 is received in needle tube 308, and the second end of needle 306 oscillates in and out of tube 308 when electromagnetic coils 301 are activated and deactivated. Accordingly, needle 306 oscillates between a first position, in which the second end of needle 306 is completely contained within needle tube 308, and a second position, in which the second end of needle 306 at least partially protrudes from needle tube 308 by a penetration depth. In some arrangements, system 300 may not include a tube but still include a skin guide (e.g., a plate sitting on the surface of skin 307), in which case needle 306 oscillates between a first position in which the tip of the needle is located on one side of the aperture (e.g., not penetrating the skin) and a second position in which the tip of the needle is located on the other side of the aperture (e.g., penetrating the skin). Although needle 306 is shown as a single needle point, it is contemplated that any tattoo needle configuration may be used, including multiple needle points mounted to a single shaft. For example, needle 306 may include a plurality of needles arranged in any of a liner, a shader, or a flat arrangement. Needle tube 308 includes user grip 309. Frame 302 is mounted to needle tube 308.

System 300 includes sensor 310. Sensor 310 is configured to scan skin 307 at the point of needle penetration. Sensor 310 provides a feedback signal to controller 311. Controller 311 is mounted to frame 302. The feedback signal relates to detected depths and thicknesses of certain layers of skin 307. Sensor 310 is configured to detect the depth and thickness of the person's epidermis, dermis, and hypodermis. Further, sensor 310 is configured to detect sub-layer depths and thicknesses within the major layers of the person's skin 307. For example, sensor 310 can determine the depth and thickness of the papillary region and the reticular region of the person's dermis at the point of needle penetration. Sensor 310 utilizes the same sensing technology as sensor 210. Accordingly, sensor 310 may utilize optical coherence tomography, ultrasound, or conductivity and/or resistance to determine skin layer thicknesses and depths based on user provided tattooing parameters and settings. Controller 311 analyzes the feedback signal from sensor 310 to determine the optimal needle penetration depth. Controller 311 is configured to adjust needle penetration depth during tattooing operations use such that ink is consistently deposited within a particular layer of skin 307, within a particular sub-layer of skin 307, at a specific depth beneath the surface of a particular layer of skin 307, within a range of a particular layer of skin 307, or at a consistent percentage of a thickness of a skin layer. Needle penetration depth is adjusted by moving frame 302 vertically up and down in small increments in relation to needle tube 308. To accomplish this adjustment, lift mechanism 312 is mounted to needle tube 308 and beneath frame 302 such that frame 302 can be displaced vertically with respect to needle tube 308. Lift mechanism 312 is capable of raising and lowering frame 302 in precise amounts (e.g., 10 or 100 μm at a time). Lift mechanism 312 may be any of a linear actuator, a piezoelectric linear actuator, a multi-layer piezoelectric linear actuator, a screw-driven actuator coupled to a stepper motor, or a combination of any of the above. The operation of lift mechanism 312 is controlled by controller 311 based on an operator programmed tattooing parameters and feedback from sensor 310.

Figure 3B:
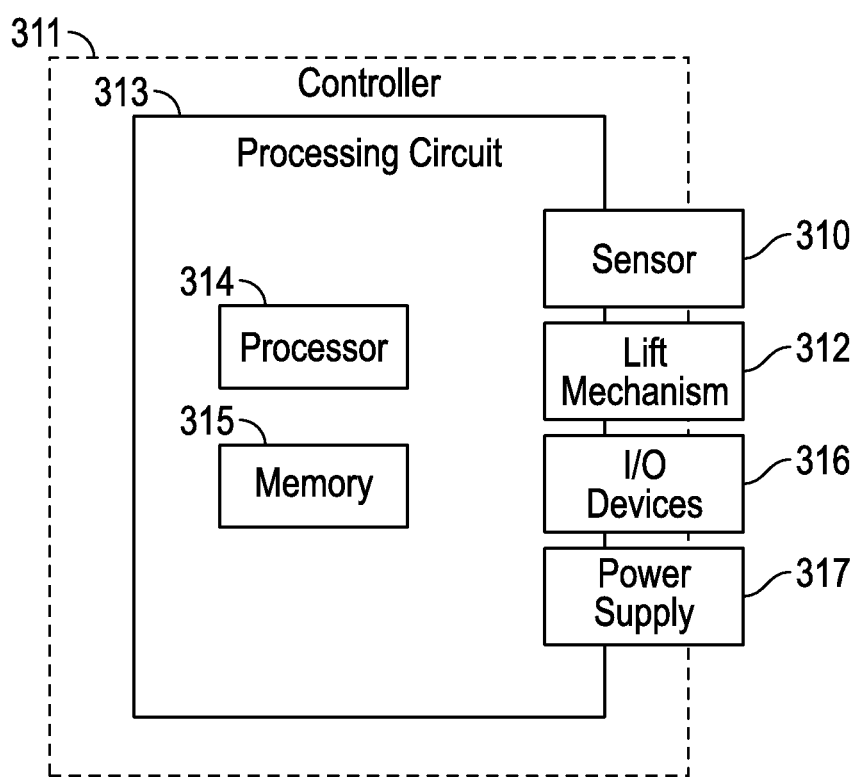
FIG. 3B is a block diagram of the second exemplary tattoo machine.

Referring to FIG. 3B, a block diagram of controller 311 is shown. Controller 311 is similar to controller 211 of system 200. Controller 311 includes processing circuit 313. Processing circuit 313 includes processor 314 and memory 315. Processing circuit 313 communicates with sensor 310, lift mechanism 312, and input/output devices 316. Controller 311 and the components of system 300 are powered by power supply 317. Memory 315 stores programming modules that, when executed by processor 314, control the operation system 300 based on desired user settings and tattooing parameters received through input/output devices 316 and skin 307 layer depth and thickness information received from sensor 310. It is contemplated that input/output devices 316 include a series of knobs, wheels, or multi-position switches (e.g., a knob, wheel, or switch for each of desired skin layer for ink placement, a depth within the desired skin layer, and any other tattooing parameter or setting). Alternatively, input/output devices 316 include a touch screen including an interactive graphical user interface such that a user of system 300 can program the desired ink placement and tattooing parameters. Still further, it is contemplated that input/output devices 316 communicate with an external computing device that a user of system 300 can program desired operation settings into (e.g., a laptop, a PDA, a smartphone, a tablet, etc.). Accordingly, the user may select the desired tattooing parameters on a smartphone and transmit the desired parameters to controller 311 via a wired or a wireless connection (e.g., Bluetooth, WiFi, etc.). Alternatively, tattooing parameters and settings are stored on removable storage media (e.g., SD, MicroSD, USB flash, etc.) and the removable storage media is provided to controller 311 through input/output devices 316. In yet another alternative, it is contemplated that memory 315 stores various tattooing templates (e.g., templates for tattooing in specified layers of skin, templates for tattooing on specified body areas, etc.). Input/output devices 316 further include a power on/off mechanism (e.g., a foot pedal or a hand operated trigger or button) such that the operator of system 300 controls when needle 306 is oscillating. Power supply 317 provides electric power to system 300. Power supply 317 may receive power from any suitable source (e.g., a rechargeable battery, a non-rechargeable battery, grid power, etc.).

In other embodiments, alternative needle drive methods can be used. One approach is to use a linear electric motor to drive the needle. The linear electric motor may also be used to retract the needle, or a passive retraction mechanism such as a spring may be employed. In such an arrangement approach, the stroke distance of the needle can be readily adjusted by controlling the actuation of the motor. Another approach is to employ fluid pressure (gas or liquid) to drive the needle, and the needle may be retracted by a spring or other mechanism.

Figure 4:
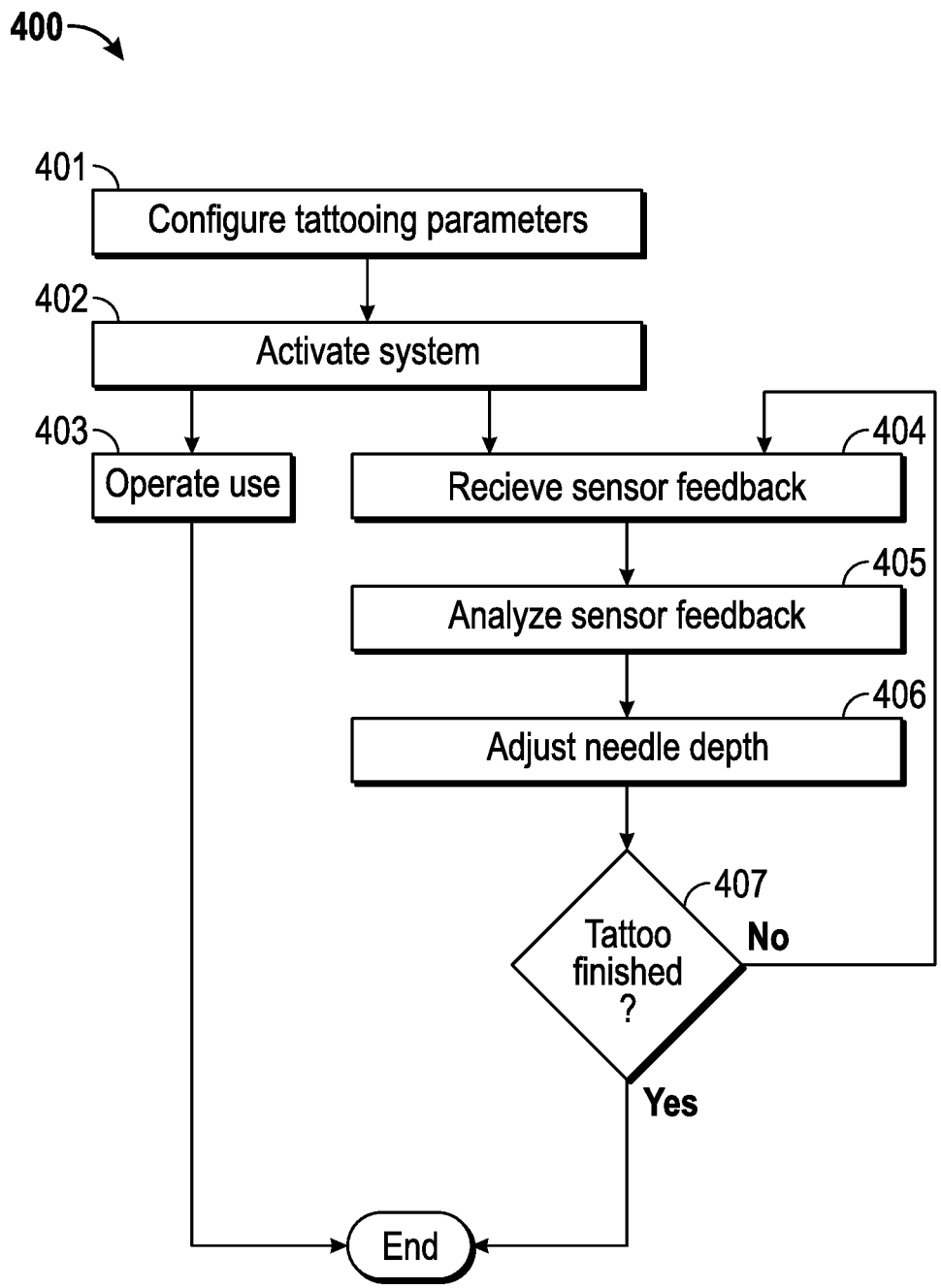
FIG. 4 is a flow diagram of a method of tattooing.

Referring to FIG. 4, a method 400 of tattooing is shown according to an exemplary embodiment. Method 400 may be used with system 200, system 300, or another similar system configured to detect skin layer depths and thicknesses and adjust a tattoo needle penetration depth based on the detected depths and thicknesses. Prior to placing a tattoo on a person, the operator of the tattooing system configures tattooing parameters for the tattooing system (step 401). The tattooing parameters include a specified skin layer or sublayer (e.g., papillary region or reticular region of the dermis) for a desired ink placement. The tattooing parameters may be more specific than a desired layer. The received tattooing parameters may include a layer and a depth within the layer (e.g., a parameter relating to placing the ink at a depth of 30% of the papillary region or 0.1 mm into the dermis). The tattooing parameters may also include information pertaining to the area of skin to be tattooed (e.g., bicep, small of the back, shoulder, etc.). The tattooing may further include a desired needle oscillation speed. Alternatively, the operator of the tattooing system may select from a set of tattoo templates (e.g., permanent tattoo on the small of the back). Each template includes preselected layer and depth information. The tattooing parameters are configured through operator interaction with a user input device. The user input device is any of a series of knobs and/or switches, a touchscreen input, a connection with a remote control device (wired or wireless), or a removable memory media (e.g., parameters stored on an SD card, a MicroSD card, or a USB flash drive and inserted into the tattooing system).

After configuring the tattooing parameters, the operator activates the tattooing system (step 402). Upon activation, a needle penetration depth is preset. The needle penetration depth is preset based on human averages for particular layers of skin (e.g., the average depth of the papillary region of the dermis). Alternatively, the needle penetration depth is adjusted once tattooing system makes contact with the person's skin. Further, upon activation, the operator power control is activated such that the operator can control when needle oscillation is occurring (e.g., through a foot pedal or a hand trigger). The operator power control is variable, which allows the operator to provide a needle speed input and vary the speed of needle oscillations. At this point, the operator of the tattooing system can begin placing the tattoo on the client (step 403).

During operator use (step 403) needle penetration depth is monitored and adjusted as necessary. Tattooing system receives feedback from a sensor (step 404). The sensor is configured to detect skin layer depths and thicknesses at or near the point of needle penetration into the skin and to provide a feedback signal relating to the detected depths and thicknesses. The sensor utilizes any of optical coherence tomography, ultrasound, or conductivity and/or resistance to determine skin layer thicknesses and depths. The sensor feedback signal is used to map the skin proximate the point of needle penetration, the map indicating the skin layer thicknesses and depths. The sensor feedback signal data may be processed by an appropriate imaging system to determine the depths and thicknesses of the layers of skin. It is contemplated that sensor feedback is actively provided throughout the duration of method 400. Alternatively, sensor feedback is provided at regular intervals based on a designated set of time (e.g., every 0.1 seconds), a set number of needle strokes (e.g., every ten needle oscillations), or after a set distance traveled across the skin (e.g., every 1 mm of needle travel). If the interval is based on the distance traveled by the tattooing system, tattooing system further includes a position or displacement sensor configured to detect the system's displacement along the skin.

A controller of the tattooing system analyzes the sensor feedback signal (step 405). In some arrangements where the feedback signal includes raw data, the controller further processes the raw data into skin layer depth and thickness measurements. As the needle travels across the skin, the distance between the outer surface of the epidermis and the desired ink placement layer will fluctuate. Accordingly, during analysis, the controller compares the current needle penetration depth with the sensor feedback data and the provided tattooing parameters. If the needle penetration depth as currently configured is too deep or too shallow to place the tattoo ink in the desired layer (or the desired portion of a layer), the controller computes the change in penetration depth that needs to be effectuated to meet the desired ink placement strategy.

Based on the sensor feedback analysis, the needle penetration depth is adjusted if necessary (step 406). The needle penetration depth is adjusted by raising or lowering the mechanism that oscillates the needle in and out of the skin (e.g., by raising and lowering motor 201 or frame 302, which houses electromagnetic coils 301). Often, the adjustment of needle penetration depth will be very slight, as the layers of the skin are very thin (e.g., the epidermis can be as thin as 0.05 mm on a human eyelid). Accordingly, the adjustment mechanism employed by the tattooing system is capable of precise amounts of movement (e.g., 10 or 100 µm at a time). The adjustment mechanism is any of a linear actuator, a piezoelectric linear actuator, a multi-layer piezoelectric linear actuator, a screw-driven actuator coupled to a stepper motor, or a combination of any of the above. The controller of the tattooing system is configured to operate the adjustment mechanism to effectuate the previously computed change in penetration depth in order to maintain the desired needle penetration depth. It is noted that in some situations, the current needle penetration depth will not require adjusting (e.g., in cases where the change in skin data is smaller than a threshold). If it is determined that no adjustment is necessary in step 405, step 406 is skipped by the tattooing system. Needle penetration adjustments are made after to a set number of needle oscillations (e.g., every oscillation, every ten oscillations, every twenty oscillations, etc.). Alternatively, needle penetration depth adjustments are made at designated of time intervals (e.g., every 0.1 seconds) or after a set distance traveled across the skin (e.g., every 1 mm of needle travel). Steps 404 through 406 are repeated throughout the duration of the tattooing operation until completion (step 407).

Figure 5A:
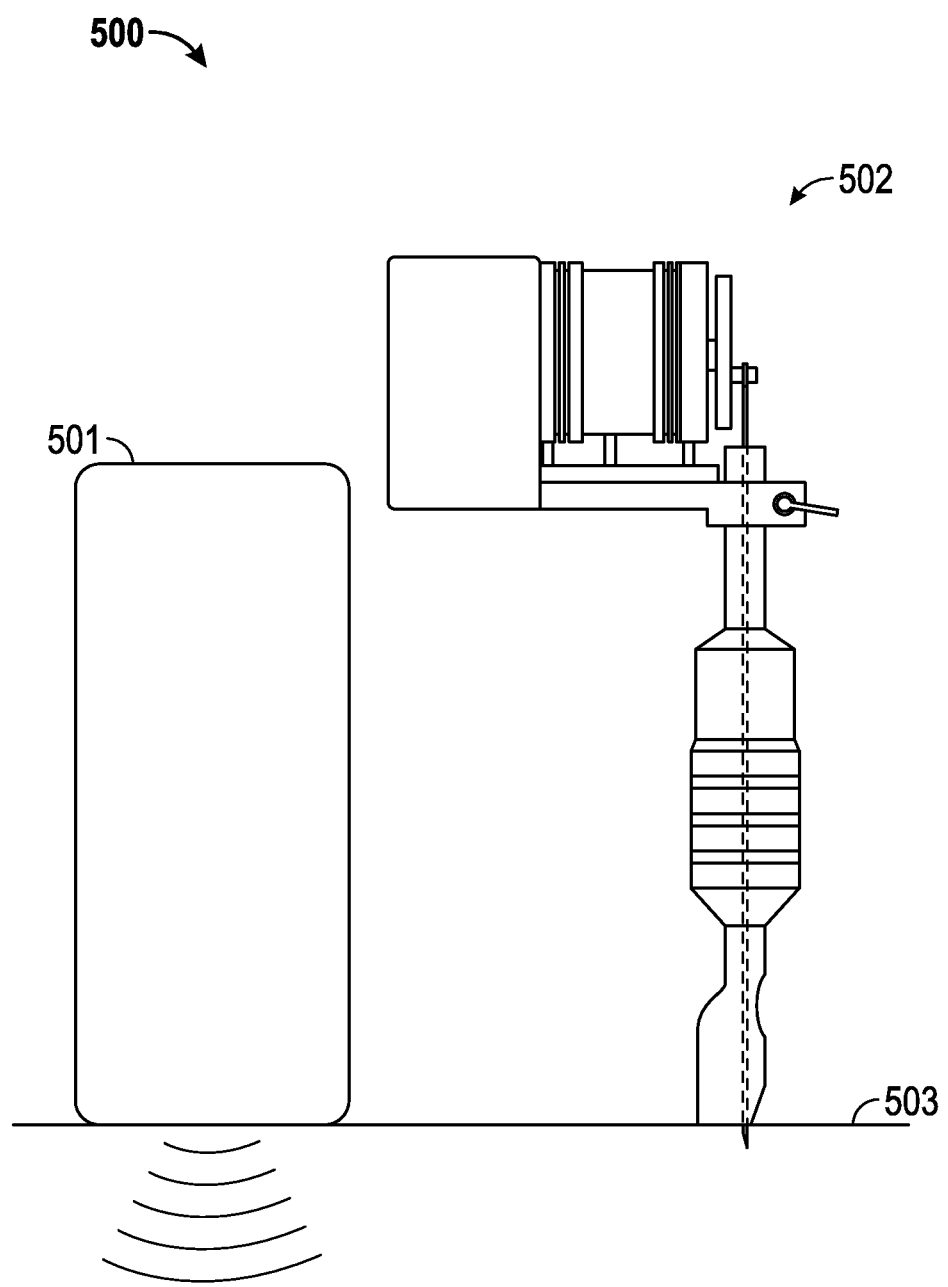
FIG. 5A is a schematic view of a skin sensor unit and tattoo unit system.

Referring to FIG. 5A, a skin mapping and tattooing system 500 is shown. System 500 generally includes sensor unit 501 and tattoo unit 502. Sensor unit 501 is configured to create a skin data of an area of skin 503 to be tattooed (e.g., create a map of skin layer thicknesses and depths at various positions along skin 503) and provides information to a tattoo machine. Generally, sensor unit 501 gathers skin data corresponding to skin 503 layer thicknesses and depths. The skin data may include skin map data corresponding to a three-dimensional map of skin 503. The skin data is then provided to tattoo unit 502, such that tattoo unit adjusts needle penetration depth based on tattoo unit 502 position as tattoo unit 502 moves along skin 503.

Figure 5B:
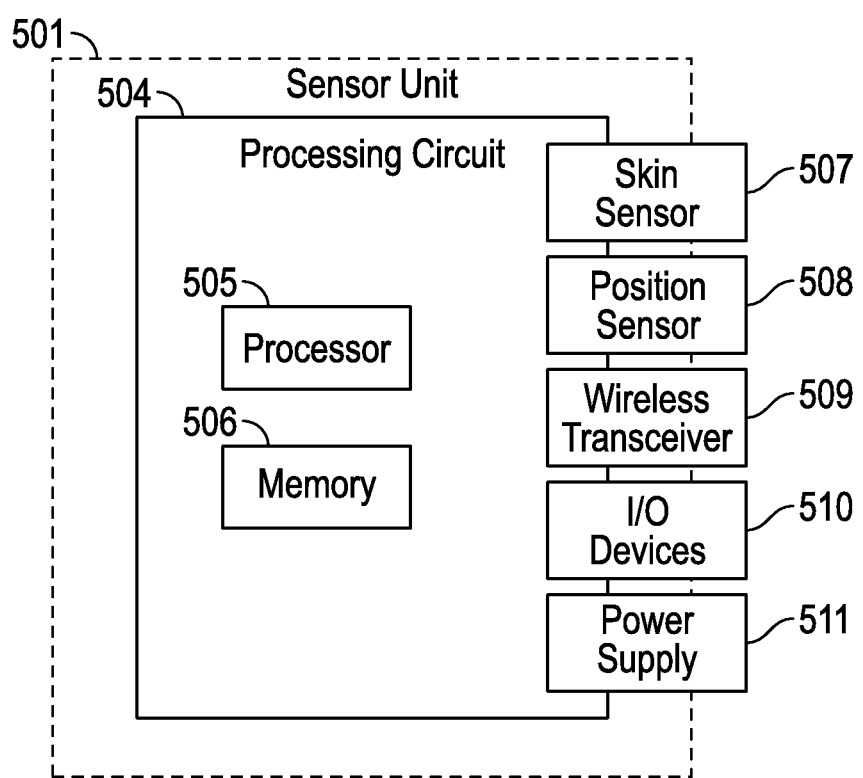
FIG. 5B is a block diagram of a skin sensor unit.

Referring to FIG. 5B, a block diagram of sensor unit 501 is shown. Sensor unit 501 includes processing circuit 504. Processing circuit 504 includes processor 505 and memory 506. Processing circuit communicates with skin sensor 507, position sensor 508, wireless transceiver 509, and input/output devices 510. Sensor unit 501 is powered by power supply 511. Memory 506 stores programming modules that, when executed by processor 505, control the operation of sensor unit 501 such that sensor unit 501 gathers skin map data corresponding to skin 503 layer thicknesses and depths. Skin sensor 507 outputs data corresponding to the detected depths and thicknesses of certain layers of skin 503. Skin sensor 507 is configured to detect the depth and thickness of the person's epidermis, dermis, and hypodermis. Further, skin sensor 507 is configured to detect sub-layer depths and thicknesses within the major layers of skin 503. For example, skin sensor 507 determines the depth and thickness of the papillary region and the reticular region of the person's dermis at the point of needle penetration. Skin sensor 507 utilizes the same sensing technology as sensor 210 and/or sensor 310. Accordingly, skin sensor 507 utilizes any of optical coherence tomography, ultrasound, or conductivity and/or resistance to determine skin layer thicknesses and depths. Position sensor 508 is a multi-axis position sensor. Position sensor 508 outputs data corresponding to the position of sensor unit 501 in relation to a reference point on skin 503. Alternatively, position sensor 508 is an absolute position sensor and outputs data corresponding to the position of sensor unit 501 in relation to a global point. Position sensor 508 data output is combined with skin sensor 507 data output to create three-dimensional map data of skin 503. Wireless transceiver 509 communicates the three-dimensional skin map data to tattoo unit 502. Wireless transceiver 509 is also configurable to communicate the three-dimensional skin map data to a central server or a host computer. In an alternate arrangement, sensor unit 501 uses a signal wire or an optical fiber to communicate the three-dimensional skin map data to tattoo unit 502. In an alternate arrangement, sensor unit 501 stores skin map data on removable storage media (e.g., SD memory card, MicroSD memory card, USB flash memory, etc.), and tattoo unit 502 is configured to receive the removable storage media to download the skin map data. Input/output devices 510 include a series of knobs, wheels, and/or multi-position switches such that a user of sensor unit 501 can instruct sensor unit to gather data pertaining to skin 503. Alternatively, input/output devices 510 include a voice recognition system, a mouse or keyboard, or a touch screen including an interactive graphical user interface. Still further, it is contemplated that input/output devices 510 communicate with an external computing device such that a user of system 500 can program desired operation settings via the external computing device (e.g., a laptop, a PDA, a smartphone, a tablet, etc.). Accordingly, the user may select the desired operational settings on the external computing device and transmit the desired operational settings to sensor unit 501 via wireless transceiver 509 or via removable storage media (e.g., SD, MicroSD, USB flash, etc.). Input/output devices 510 further includes a power on/off mechanism such that the operator can turn on/off sensor unit 501. Power supply 511 provides electric power to sensor unit 501. Power supply 511 may receive power from any suitable source (e.g., a rechargeable battery, a non-rechargeable battery, grid power, etc.).

Figure 5C:
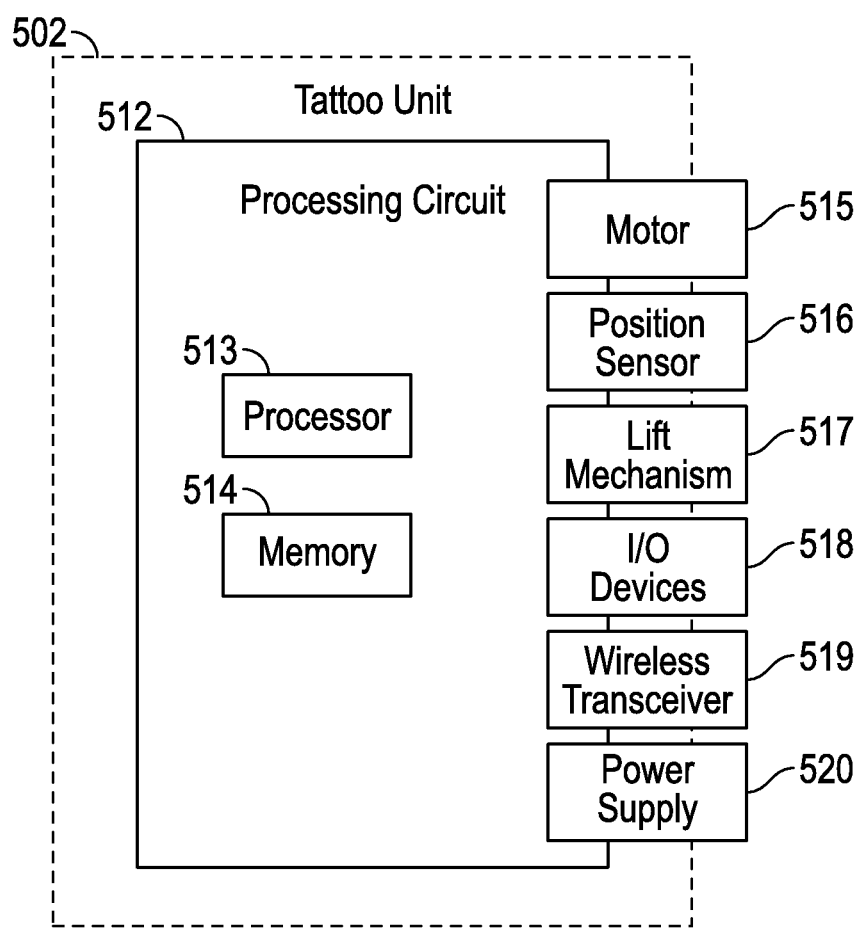
FIG. 5C is a block diagram of a tattoo unit.

Referring to FIG. 5C, a block diagram of tattoo unit 502 is shown. Tattoo unit 502 includes processing circuit 512. Processing circuit 512 includes processor 513 and memory 514. Processing circuit 512 communicates with motor 515, position sensor 516, lift mechanism 517, input/output devices 518, and wireless transceiver 519. Tattoo unit is powered by power supply 520. Memory 514 stores programming modules that, when executed by processor 513, control the operation of tattoo unit 502 on desired user settings received through input/output devices 518 and skin map data received from sensor unit 501. Position sensor 516 is a multi-axis position sensor. Position sensor 516 outputs data corresponding to the position of tattoo unit 502 in relation to a point on skin 503. Alternatively, position sensor 516 is an absolute position sensor and outputs data corresponding to the position of tattoo unit 502 in relation to a global point. Position sensor 516 data output is compared to skin map data received from sensor unit 501, such that needle penetration depth is adjusted via lift mechanism 517 to deposit ink at the desired position within skin 503. Wireless transceiver 519 communicates sensor unit 501 wireless transceiver 509, such that tattoo unit 502 receives skin map data from sensor unit 501. Wireless transceiver 519 is also configurable to communicate with a central server or host computer that hosts the skin map data. In an alternate arrangement, tattoo unit 502 is configured to receive skin map data via wire, an optical fiber, or removable storage media (e.g., SD memory card, MicroSD memory card, USB flash memory, etc.). Input/output devices 518 include a series of knobs, wheels, and/or multi-position switches (e.g., a knob, wheel, or switch for each of motor 515 speed, desired skin 503 layer for ink placement, and a depth within the desired skin 503 layer). Alternatively, input/output devices 510 include a voice recognition system, a mouse or keyboard, or a touch screen displaying an interactive graphical user interface such that a user of tattoo unit 502 can program the desired tattooing parameters, including an ink placement strategy and motor 515 speed parameters. Still further, it is contemplated that input/output devices 518 communicate with an external computing device that a user of system 500 can program desired tattooing parameters and settings into tattoo unit 502 (e.g., a laptop, a PDA, a smartphone, a tablet, etc.). Accordingly, the user may select the desired tattooing parameters via the external computing device and transmit the desired parameters to tattoo unit 502 via wireless transceiver 519. Still further, it is contemplated that tattoo unit 502 is configured to receive the desired tattooing parameters on removable storage media (e.g., SD, MicroSD, USB flash, etc.). In yet another alternative, it is contemplated that memory 514 stores various tattooing templates (e.g., templates for tattooing in specified layers of skin, templates for tattooing on specified body areas, etc.). Input/output devices 518 further includes a motor 515 on/off mechanism (e.g., a foot pedal or a hand operated trigger or button) such that the operator of tattoo unit 502 controls when the needle is oscillating. The on/off mechanism is capable of instructing variable speeds for motor 515 (e.g., a pressure sensitive foot pedal or hand trigger). Tattoo unit 502 is drawn as a rotary tattoo machine (e.g., system 200).

However, it should be understood that tattoo unit 502 can also be an electromagnetic tattoo machine (e.g., system 300) or any other form of tattoo machine operable to place ink at a controllable depth within layers of skin. Power supply 520 provides electric power to tattoo unit 502. Power supply 520 may receive power from any suitable source (e.g., a rechargeable battery, a non-rechargeable battery, grid power, etc.).

Figure 6:
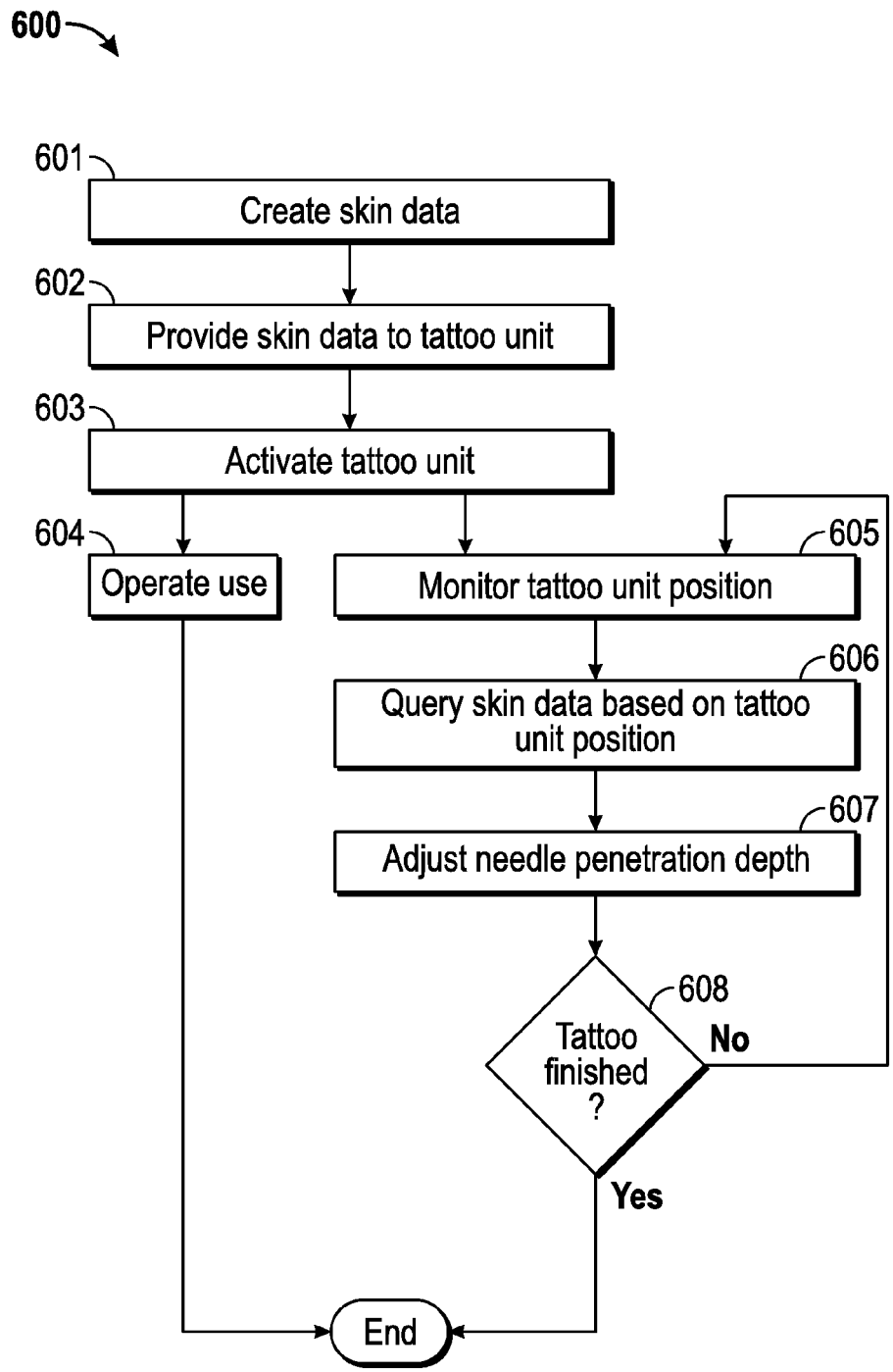
FIG. 6 is a flow diagram of a method of tattooing.

Referring to FIG. 6, a method 600 of tattooing is shown according to an exemplary embodiment. It is contemplated that method 600 is employed by system 500 or another tattooing system having a separate sensor unit (e.g., sensor unit 501) and tattoo unit (e.g., tattoo unit 502). First, skin data is created (step 601). Skin data includes skin map data corresponding to a three-dimensional map of an area of skin to be tattooed. The three-dimensional map includes data pertaining to detected depths and thicknesses of the layers of skin at various points across the area of skin to be tattooed. Skin data is created through the use of a stand-alone sensor unit (e.g., sensor unit 501). The sensor unit includes a skin sensor and a position sensor. The skin sensor is configured to detect the depth and thickness of the person's epidermis, dermis, and hypodermis. Further, the skin sensor is configured to detect sub-layer depths and thicknesses within the major layers of skin. For example, the skin sensor may determine the depth and thickness of the papillary region and the reticular region of the person's dermis at the point of needle penetration. The skin sensor utilizes any of optical coherence tomography, ultrasound, or conductivity and/or resistance to determine skin layer thicknesses and depths. Skin data is tagged with position data from a position sensor. The position sensor is a multi-axis position sensor that outputs data corresponding to the position of the sensor unit in relation to a point on skin. The user programs a reference point of the skin into sensor unit. The reference point is marked such that the tattoo unit can later be aligned to the same reference point. The reference point serves as a base point for the position sensor of the sensor unit and the position sensor of the tattoo unit. The reference point also serves as a base point for the tattoo unit. Alternatively, the position sensor is an absolute position sensor and outputs data corresponding to the position of the sensor unit in relation to a global reference point. The position data received from the position sensor is combined with the sensor data received from the skin sensor and is processed into a three-dimensional map data of the skin to be tattooed. Map processing is performed by the sensor unit, by an external processing system (e.g., an external computing device), or by the tattoo unit.

Next, the skin data is provided to the tattoo unit (step 602). Skin data is wirelessly sent to the tattoo unit from the sensor unit. The tattoo unit and the sensor unit each include a wireless transceiver that communicates directly with each other (e.g., skin map data is sent directly from the sensor unit to the tattoo unit) or indirectly (e.g., skin map data is routed from the sensor unit, through a router, and to the tattoo unit; skin map data is first sent to a host computer or a server (e.g., an external map processing machine, cloud server, etc.), and tattoo unit queries the host computer or server to download the skin map data). Alternatively, the skin map data is stored on removable storage media (e.g., SD memory card, MicroSD memory card, USB flash memory, etc.), and the tattoo unit is configured to receive the removable storage media to download the skin map data.

After receiving the skin data, the operator of the tattooing system activates the tattoo unit (step 603). During tattoo unit activation, the operator of tattoo unit configures tattooing parameters for the tattoo unit. The tattooing parameters include a specified skin layer (e.g., papillary region or reticular region of the dermis) for a desired ink placement. The tattooing parameters may include additional information to the desired skin layer. For example, received tattooing parameters may include a layer and a depth within the layer (e.g., a parameter relating to placing the ink at a depth of 30% of the papillary region or 0.1 mm into the dermis). The tattooing parameters can also include information pertaining to the area of skin to be tattooed (e.g., bicep, small of the back, shoulder, etc.) and/or a desired needle oscillation speed. Alternatively, the operator of the tattooing system can select from a set of tattoo templates (e.g., permanent tattoo on the small of the back). Each template includes preselected layer and depth information. The operator configures the tattooing parameters through with a user input device. The user input device is any of a series of knobs and/or switches, a touchscreen input, a connection with a remote control device (wired or wireless), or removable memory input (e.g., parameters stored on an SD card, a MicroSD card, or a USB flash drive and inserted into the tattooing system). Further, upon activation, a needle penetration depth is preset. The needle penetration depth is preset based on human averages for particular layers of skin (e.g., the average depth of the papillary region of the dermis). Alternatively, the needle penetration depth is set once the tattoo unit makes contact with the person's skin. Further, upon activation, the operator power control is activated such that the operator controls when needle oscillation is occurring (e.g., through a foot pedal or a hand trigger). After the initial setup, the operator of the tattoo unit begins using the tattoo unit (step 604).

During tattoo unit use, the position of tattoo unit, and thus the position of the needle, is monitored (step 605). As the needle travels across the skin, the distance between the outer surface of the epidermis and the desired ink placement layer will fluctuate. Accordingly, the position of the tattoo unit is measured through a position sensor. The position sensor is a multi-axis position sensor that outputs data corresponding to the position of the sensor unit in relation to a reference point on skin. The tattoo unit is initially placed at the same reference point that was previously marked during skin mapping in step 601. The user indicates that the tattoo unit is at the reference point, and the tattoo unit compares its position with the skin map data as the tattoo unit is moved along the skin. Alternatively, the position sensor is an absolute position sensor and outputs data corresponding to the position of the sensor unit in relation to a global reference point. In either arrangement, the tattoo unit is configured to query the skin data based on its detected position to determine the previously detected skin layer depths and thicknesses at the point of needle penetration into the skin (step 606).

Based on the skin layer depth and thickness data returned in step 606, needle penetration depth is adjusted as necessary (step 607). Accordingly, the current needle penetration depth is compared to the tattooing parameters relating to where ink is to be placed and to the layer depth information provided by the skin map data. If the needle penetration depth is too deep or too shallow to place the tattoo ink in the desired layer (or the desired portion of a layer), the needle penetration depth is adjusted such that ink is placed at the appropriate location within the skin. The needle penetration depth is adjusted by raising or lowering the mechanism that oscillates the needle in and out of the skin (e.g., by raising and lowering motor 515, motor 201, or frame 302, which houses electromagnetic coils 301). Often, the adjustment of needle penetration depth will be very slight, as the layers of the skin are very thin (e.g., the epidermis can be as thin as 0.05 mm on a human eyelid). Accordingly, the adjustment mechanism (e.g., lift mechanism 517) employed by the tattoo unit is capable of precise amounts of movement (e.g., 10 or 100 µm at a time). The adjustment mechanism is any of a linear actuator, a piezoelectric linear actuator, a multi-layer piezoelectric linear actuator, a screw-driven actuator coupled to a stepper motor, or a combination of any of the above. The tattoo unit is configured to operate the adjustment mechanism to achieve the desired adjustment to the needle penetration depth. It is noted that in some situations, the current needle penetration depth will not require adjusting. If it is determined that no adjustment is necessary in step 607, step 607 is skipped by the tattoo unit. Needle penetration adjustments are made after a set number of needle oscillations (e.g., every oscillation, every ten oscillations, ever twenty oscillations, etc.), at designated time intervals (e.g., every 0.1 seconds), or after a displacement by a set lateral distance of needle travel (e.g., every 1 mm). Steps 605 through 607 are repeated throughout the duration of the tattooing operation until completion (step 608).

Figure 7:
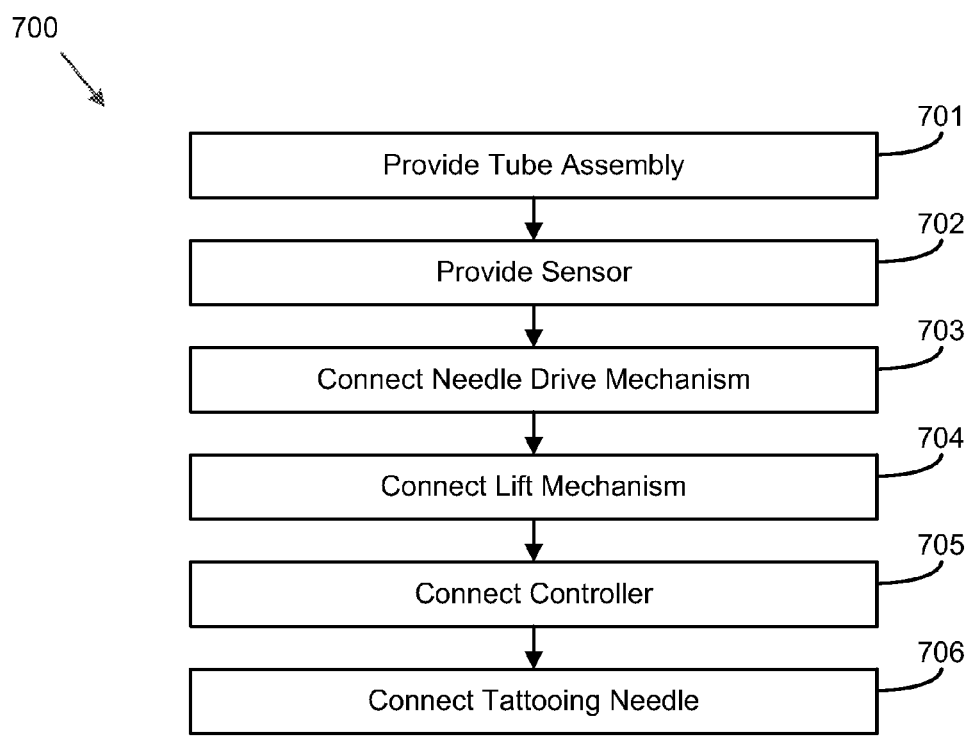
FIG. 7 is a flow diagram of a method of making a tattooing device.

Referring to FIG. 7, a method of making a tattooing device (e.g., system 200, system 300, system 500, etc.) is shown according to an exemplary embodiment. Method 700 begins when a tube assembly is provided (step 701). The tube assembly includes a tube which will ultimately receive a tattooing needle. The tube assembly may include a guide portion configured to allow the tattooing device to rest on the top of a person's skin. Alternatively, a separate guide may be connected (e.g., screwed, glued, or otherwise coupled) to the tube assembly. Additionally, the tube assembly may include a grip configured such that an operator of the tattooing device can hold the tattooing device while depositing ink into a person's skin. The grip may be removably connected to the tube assembly, in which case the grip must be connected to the tube assembly during assembly.

A sensor is provided (step 702). The sensor may be connected to the tube assembly (e.g., mounted to the tube assembly or integrated into the guide). In an alternative arrangement, the sensor is a stand-alone sensor unit (e.g., sensor unit 501). The sensor may be any of the above sensors described with respect to systems 200, 300, and/or 500 (e.g., an ultrasound sensor, an optical coherence tomography sensor, a skin conductivity sensor, a skin resistance sensor, etc.). As in the above described systems, the sensor is configured to output a feedback signal relating to a detected skin characteristic (e.g., a skin layer depth and thickness) to a controller of the tattooing device.

A needle drive mechanism is connected to the tube assembly (step 703). The needle drive mechanism is configured to move a needle between a first position in which the needle is contained within the tube assembly, and a second position in which the needle at least partially protrudes from the tube assembly by a penetration depth. In some arrangements, the system may not include a tube but includes a skin guide (e.g., a plate sitting on the surface of the skin), in which case the needle oscillates between a first position in which the tip of the needle is located on one side of the aperture (e.g., not penetrating the skin) and a second position in which the tip of the needle is located on the other side of the aperture (e.g., penetrating the skin). The needle drive mechanism may include a motor and an offset camshaft (e.g., as described above with respect to system 200). Alternatively, the needle drive mechanism may include at least one electromagnetic coil (e.g., as described above with respect to system 300). The needle drive mechanism may be adjustable such that it can oscillate the needle in and out of the tube at a variable speed.

A lift mechanism is connected to the tube assembly (step 704). The lift mechanism is configured to adjust a needle penetration depth. The lift mechanism may be any of the above described lift mechanisms of systems 200, 300, and/or 500. The lift mechanism may be connected to the tube assembly. The lift mechanism may be connected to the tube assembly between the needle drive mechanism and the tube assembly such that the lift mechanism can displace the needle drive mechanism with respect to tube assembly. The lift mechanism is responsive to commands from the controller of the tattooing device.

A controller is operatively coupled to the tattooing device (step 705). The controller is configured to control the operation of the tattooing device in the same manner as the controllers and processing circuits discussed above with respect to systems 200, 300, and/or 500. The controller is operatively connected to the sensor such that it receives the sensor feedback signal. The controller is operatively connected to the lift mechanism such that the controller is configured to cause the lift mechanism to adjust the needle penetration depth based on the feedback signal received from the sensor. In some arrangements, the controller is operatively connected to the needle drive mechanism. The controller may be configured to adjust the oscillation speed of the needle and toggle operating power to the needle drive mechanism. The controller may additionally be configured to receive a user input (e.g., an on/off switch, an operating trigger, etc.).

A needle is connected to the needle drive mechanism (step 706). The needle may be any of the tattooing needles described in this application (e.g., a single point, a bar needle, a filler needle, etc.). A first end of the needle is connected to the needle drive mechanism. The body of the needle is placed within the tube of the tube assembly. A second end of the needle is arranged to oscillate in and out of the tube between a first position in which the needle is contained within the tube assembly, and a second position in which the needle at least partially protrudes from the tube assembly by a penetration depth.

It is contemplated that any of the above tattooing systems and methods can be used to provide long-term temporary tattoos Ink deposited in the lower layers of the epidermis will migrate to the surface of the skin and fall off of the body with dead skin cells through keratinization. Typically, skin cells from the lowest layer of the epidermis complete the keratinization process in about twenty-eight days. Thus, a person can have a temporary tattoo that lasts for a duration of approximately four weeks if ink is deposited by a tattoo machine in the lowest layer of the epidermis. To achieve the temporary tattoo, the tattoo needle penetration depth is set to the bottom portion of the epidermis. It is contemplated that the tattoo machine operator may set the tattoo needle penetration depth to a more conservative depth (e.g., 80% of the depth of the epidermis) to avoid accidentally depositing ink into the more permanent dermis layer of the skin. Further, it is contemplated that the needle penetration depth is selected based on the desired time length for the temporary tattoo. For example, a person may wish to have a tattoo for only a week, not four weeks. Accordingly, the needle penetration depth is shortened to approximately 25% of the epidermis. The shallower the tattoo machine needle penetration, the shorter the duration of the tattoo.

Use of the above tattooing systems and methods is not limited to tattoo operations performed on people. Tattoos may be applied with the above systems and methods to animals. For example, a farmer may use any of the above systems and methods to mark livestock. Further, the above systems and methods may be used for medical fluid deliveries into specific layers of skin. For example, a doctor may use any of the above systems and methods to deliver an intradermal or subcutaneous injection of a medicine in the appropriate layer of a patient's skin.

It is important to note that the construction and arrangement of the elements of the systems and methods as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the enclosure may be constructed from any of a wide variety of materials that provide sufficient strength or durability, and in any of a wide variety of colors, textures, and combinations. Additionally, in the subject description, the word "exemplary" is used to mean serving as an example, instance, or illustration. Any embodiment or design described herein as "exemplary" is not necessarily to be construed as preferred or advantageous over other embodiments or designs. Rather, use of the word "exemplary" is intended to present concepts in a concrete manner. Accordingly, all such modifications are intended to be included within the scope of the present inventions. The order or sequence of any process or method steps may be varied or re-sequenced according to alternative embodiments. Any means-plus-function clause is intended to cover the structures described herein as performing the recited function and not only structural equivalents but also equivalent structures. Other substitutions, modifications, changes, and omissions may be made in the design, operating conditions, and arrangement of the preferred and other exemplary embodiments without departing from scope of the present disclosure or from the spirit of the appended claims.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures, and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps, and decision steps.

What is claimed is:

1. A tattooing apparatus, comprising:
   a needle having at least one tip, wherein the needle is configured to move between a first position in which the tip is located above the surface of a skin, and a second position in which the tip is located at a penetration depth underneath the skin surface, and wherein the needle is further configured to deposit an ink between the skin surface and the penetration depth;
   a needle drive mechanism configured to move the needle between the first position and the second position;
   a sensor configured to output a feedback signal corresponding to a skin thickness characteristic, wherein the skin thickness characteristic includes a detected depth and thickness of a dermis layer of the skin, wherein the dermis layer of the skin has a fluctuating detected depth and thickness; and
   a controller configured to receive the feedback signal, wherein the controller is configured to automatically adjust the penetration depth based on the skin thickness characteristic to account for the fluctuating detected depth and thickness such that the ink is deposited at a specified depth within the dermis layer of the skin, wherein the specified depth is a consistent percentage of the thickness of the dermis layer of the skin.

2. The apparatus of claim 1, wherein in the first position the needle is contained within a tube, and in the second position the tip of the needle protrudes from the tube by a distance at least that of the penetration depth.

3. The apparatus of claim 1, wherein in the first position the tip of the needle is located on one side of an aperture of a skin guide or plate or tube, and in the second position the needle protrudes at least partially through the aperture such that the tip of the needle is a distance at least that of the penetration depth past the aperture.

4. The apparatus of claim 1, wherein the controller is configured to adjust the penetration depth such that the needle deposits the ink in the dermis layer throughout a tattooing operation.

5. The apparatus of claim 4, wherein the controller is configured to adjust the penetration depth such that the needle deposits the ink in a papillary sub-layer of the dermis layer throughout the tattooing operation.

6. The apparatus of claim 1, wherein the sensor is an ultrasound sensor.

7. The apparatus of claim 1, wherein the sensor is an optical coherence tomography sensor.

8. The apparatus of claim 1, wherein the sensor utilizes a skin conductivity or a skin resistance to detect the skin characteristic.

9. The apparatus of claim 1, further comprising a lift mechanism configured to increase or decrease the penetration depth.

10. The apparatus of claim 9, wherein the lift mechanism is configured to move the needle drive mechanism relative to a surface of the skin.

11. The apparatus of claim 1, wherein the needle drive mechanism includes a motor and an offset camshaft, wherein a first end of the needle attaches to the offset camshaft.

12. The apparatus of claim 1, further comprising a displacement sensor configured to detect a distance the needle is displaced along a surface of the skin.

13. The apparatus of claim 12, wherein the controller is configured to adjust the penetration depth after a set needle displacement distance.

14. The apparatus of claim 12, wherein the sensor is configured to detect the skin thickness characteristic after a set needle displacement distance.

15. The apparatus of claim 1, further comprising a user input device configured to receive a user input corresponding to a desired tattoo characteristic.

16. The apparatus of claim 15, wherein the desired tattoo characteristic includes a skin layer where the ink is to be deposited.

17. The apparatus of claim 1, wherein the controller is configured to adjust the penetration depth when a difference between the detected skin thickness characteristic and a stored skin thickness characteristic exceeds a threshold.

18. A tattooing system, comprising:
- a sensor unit configured to provide skin data corresponding to an area of skin, wherein the skin data includes a sensed skin characteristic of the area of skin, and wherein the sensed skin characteristic includes a detected depth and thickness of a dermis layer of the area of skin, wherein the dermis layer of the area of skin has a fluctuating detected depth and thickness; and
- a tattoo unit, wherein the tattoo unit is separate from the sensor unit, the tattoo unit including:
  - a needle having at least one tip, wherein the needle is configured to move between a first position in which the tip is located above a surface of the skin, and a second position in which the tip is located at a penetration depth underneath the skin surface, and wherein the needle is further configured to deposit an ink between the skin surface and the penetration depth;
  - a needle drive mechanism configured to move the needle between the first position and the second position;
  - a tattoo unit position sensor configured to output a signal corresponding to a position of the tattoo unit on the area of skin;
  - a controller configured to automatically adjust the penetration depth based on the position of the tattoo unit and on the skin data based on the sensed skin characteristic to account for the fluctuating detected depth and thickness such that the ink is deposited at a specified depth within the dermis layer of the area of skin, wherein the penetration depth causes the needle to penetrate to a consistent percentage of the thickness of the dermis layer of the skin.

19. The system of claim 18, wherein the tattoo unit position sensor is a relative position sensor that measures the position of the tattoo unit relative to a reference point of the area of skin.

20. The system of claim 19, wherein the sensor unit includes a sensor unit position sensor.

21. The system of claim 20, wherein the sensor unit position sensor is a relative position sensor that measures the position of the sensor unit relative to the reference point of the area of skin.

22. The system of claim 18, wherein the sensor unit includes an ultrasound sensor.

23. The system of claim 18, wherein the sensor unit includes an optical coherence tomography sensor.

24. The system of claim 18, wherein the sensor unit senses a skin conductivity or a skin resistance.

25. The system of claim 18, wherein the tattoo unit further comprising lift mechanism configured to increase or decrease the penetration depth.

26. The system of claim 18, wherein the controller is configured to adjust the penetration depth after a change in the detected skin data exceeds a threshold.

27. The system of claim 18, further comprising a user input device configured to receive a user input corresponding to a desired tattoo characteristic.

28. The system of claim 27, wherein the desired tattoo characteristic includes a skin layer where the ink is to be deposited.

29. The system of claim 28, wherein the skin layer has a skin layer depth and a skin layer thickness, and the skin data includes information about the skin layer depth and the skin layer thickness at various points across the area of skin.

30. The system of claim 29, wherein the controller is configured to adjust the penetration depth such that the needle penetrates the skin into the skin layer, but not beyond the skin layer at all positions within the area of skin.

* * * * *